United States Patent
Qi

(10) Patent No.: US 9,605,578 B1
(45) Date of Patent: Mar. 28, 2017

(54) PARTICULATE MATTER SENSING DEVICE FOR CONTROLLING AND DIAGNOSING DIESEL PARTICULATE FILTER SYSTEMS

(71) Applicant: Baohua Qi, Marietta, GA (US)

(72) Inventor: Baohua Qi, Marietta, GA (US)

( * ) Notice: Subject to any disclaimer, the term of this patent is extended or adjusted under 35 U.S.C. 154(b) by 7 days.

(21) Appl. No.: 14/956,898

(22) Filed: Dec. 2, 2015

(51) Int. Cl.
    *F01N 3/00*     (2006.01)
    *F01N 9/00*     (2006.01)
    *F01N 3/023*     (2006.01)
    *G01N 15/06*     (2006.01)
    *G01M 15/10*     (2006.01)
    *G01N 15/00*     (2006.01)

(52) U.S. Cl.
    CPC ............ *F01N 9/002* (2013.01); *F01N 3/023* (2013.01); *G01M 15/102* (2013.01); *G01N 15/0656* (2013.01); *F01N 2900/0416* (2013.01); *G01N 2015/0046* (2013.01)

(58) Field of Classification Search
    USPC .............. 60/274, 275, 276, 295, 297, 311; 73/28.01, 28.02, 335.03, 31.07, 114.71
    See application file for complete search history.

(56) References Cited

U.S. PATENT DOCUMENTS

| | | | | |
|---|---|---|---|---|
| 8,176,768 B2* | 5/2012 | Kondo | ............... | G01N 15/0656 73/23.33 |
| 8,382,884 B2* | 2/2013 | Okayama | ........... | G01N 15/0656 60/275 |
| 8,823,400 B2* | 9/2014 | Hocken | ............... | F02D 41/1466 324/691 |
| 8,860,439 B2* | 10/2014 | Kimata | ................... | F01N 11/00 324/464 |
| 9,528,971 B2* | 12/2016 | Teranishi | ........... | G01N 33/0047 |
| 2012/0266646 A1* | 10/2012 | Maeda | ................ | F02D 41/1466 73/1.06 |

\* cited by examiner

*Primary Examiner* — Binh Q Tran

(57) ABSTRACT

A PM sensing device including a front sensing piece receiving an exhaust flow, a back sensing piece posited downstream from the front sensing piece, and a sensor controller electrically connected to the sensing pieces for measuring their impedances and calculate a PM sensing value accordingly. The PM sensing device has two operating modes: an impedance measurement mode, in which a PM sensing value is calculated, and a regeneration mode, in which accumulated PM is removed. Since PM is only deposited in the front sensing piece, by comparing impedances of the front and the back sensing pieces, PM sensing values can be obtained insensitive to particle size, exhaust gas temperature, and exhaust gas species. When the PM sensor is positioned in a DPF system, sensor regeneration times in a predetermined period of time after a DPF regeneration completes can be used for triggering a new DPF regeneration and detecting DPF failures.

20 Claims, 18 Drawing Sheets

PARTICULATE MATTER SENSING DEVICE FOR CONTROLLING AND DIAGNOSING DIESEL PARTICULATE FILTER SYSTEMS

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

TECHNICAL FIELD OF THE INVENTION

This present application claims priority from U.S. provisional application No. 62/087,461 having the same title as the present invention and filed on Dec. 4, 2014.

This invention relates to an apparatus and method for detecting a Particulate Matters (PM) amount in an exhaust gas flow generated from engine and issues in an exhaust gas processing system for removing PM in the exhaust gas flow, more specifically, to an apparatus and method for detecting a PM amount in an exhaust flow generated from an internal combustion engine and issues in a Diesel Particulate Filter (DPF) system for removing PM in the exhaust flow.

BACKGROUND OF THE INVENTION

Environmentally harmful species in the exhaust gas emitted from an internal combustion engine, such as hydrocarbons (HC), carbon monoxide (CO), PM, and nitric oxides (NOx) are regulated species that need to be removed from the exhaust gas. In lean combustion engines, e.g. diesel engines, determined by their lean combustion nature, PM and NOx are two major emissions. In controlling these emissions, DPF has become the most effective technology in decreasing PM emissions, including both particle mass and numbers, while a number of technologies, including LNT (Lean NOx Trap) and SCR (Selective Catalytic Reduction) have been used for reducing NOx emissions.

In a DPF system, PM information is important in controlling DPF regeneration processes and detecting anomalies in the DPF system. Normally DPF systems need to be regenerated from time to time to remove accumulated PM. In triggering a DPF regeneration process, PM deposit quantity is required to be accurately detected to avoid late regeneration which may cause damage to the DPF due to that a large amount of extra heat can be generated in self-sustained combustion of PM in the DPF. In running a DPF system, in addition to PM deposit quantity, the effectiveness of the DPF, which is indicated by a filtering efficiency, also needs to be monitored. A low filtering efficiency suggests a DPF failure, which is required to be detected to satisfy On Board Diagnostic (OBD) requirements.

The PM deposit quantity can be detected directly or calculated with a PM concentration in exhaust gas flow upstream from the DPF, while a low filtering efficiency can be detected by monitoring PM concentration downstream from the DPF. A variety of sensors, such as capacitive sensors and microwave sensors can be used in directly detecting PM deposit amount in a DPF, while resistive sensors and charge transient sensors are used in detecting PM concentration in an exhaust flow. Among these sensors, PM deposit sensors normally are not appropriate for diagnosing DPF failures, while PM concentrations sensors are sensitive to particulate size and their poor accuracy limits their applications in controlling DPF regenerations.

To increase control and diagnostic performance whilst lower system complexity, it is then a primary object of the present invention to provide a multifunctional PM sensing device that is insensitive to particulate size and other influencing factors, such as exhaust gas temperature and exhaust gas species, and can be used for both triggering DPF regeneration and detecting DPF failures.

A further object of the present invention is to provide a PM sensing device that is able to regenerate by itself, so that a PM concentration in a shorter period of time can be obtained.

Another object of the present invention is to provide a diagnostic apparatus with a PM sensing device to detect anomalies in a DPF system and a DPF device.

BRIEF SUMMARY OF THE INVENTION

The present invention provides a PM sensing device including a front sensing piece receiving an exhaust flow, a back sensing piece positioned downstream from the front sensing piece, and a sensor controller electrically connected to the sensing pieces for measuring their impedances and calculate a PM sensing value accordingly. In an embodiment, the front sensing piece includes a front particulate filter piece positioned in between a first electrode and a second electrode, while the back sensing piece has a back particulate filter piece positioned in between a third electrode and the second electrode. The electrodes are electrically connected to the sensor controller. In an impedance measurement mode, an impedance in between the first electrode and the second electrode, Zf, is measured together with an impedance in between the third electrode and the second electrode, Zb. And a PM sensing value is calculated with the Zf and Zb values. In this sensor, since PM is filtered by the front particulate filter piece, by comparing Zf and Zb values, the PM sensing value can be obtained insensitive to particle size, exhaust gas temperature, and exhaust species. In addition to measuring impedance, regenerating the sensing pieces is also needed to remove accumulated PM. In a sensor regeneration mode, the resistances of the electrodes are measured, and a temperature in the sensing pieces is calculated with the measured resistance values. The temperature is controlled within a predetermined range with a PWM control signal applied to the second electrode, and a closed-loop control including a feed-back loop and a feed-forward loop is used for the temperature control.

The calculated PM sensing value is indicative of a PM deposit quantity in the front particulate filter piece. If the PM sensor is positioned upstream from a DPF, and the DPF and the front particulate filter piece have the same wall-flow structure, then the PM sensing value is also indicative of a PM deposit amount in the DPF. Furthermore, when the PM sensor is regenerated after the PM sensing value is above a predetermined threshold, the sensor regeneration frequency can be used as an indication of PM concentration.

With the PM sensing values and regeneration frequency, the PM sensor can be used for triggering DPF regenerations and detecting DPF failures. In an exemplary application, the PM sensor is positioned upstream from a DPF, and sensor regeneration times in a predetermined period of time after a DPF regeneration completes is used for triggering a new DPF regeneration. In another exemplary application, the PM sensor is positioned downstream from a DPF, and both of a sensor regeneration number and a ratio of the sensor regeneration number to a total fueling amount in a predetermined period of time, after a DPF regeneration completes, are used for detecting DPF system failures. The PM sensor can also be used for detecting failures in DPF devices. In another exemplary application, a first PM sensor is positioned upstream from a DPF, and a second one is positioned downstream from the DPF. After a DPF regeneration completes, a difference between the sensor regeneration numbers of the upstream and the downstream PM sensors in a predetermined period of time is an indication of the DPF filtering efficiency. A DPF fault is triggered if this difference value is lower than a predetermined threshold.

DETAILED DESCRIPTION OF THE INVENTION

Figure 1A:
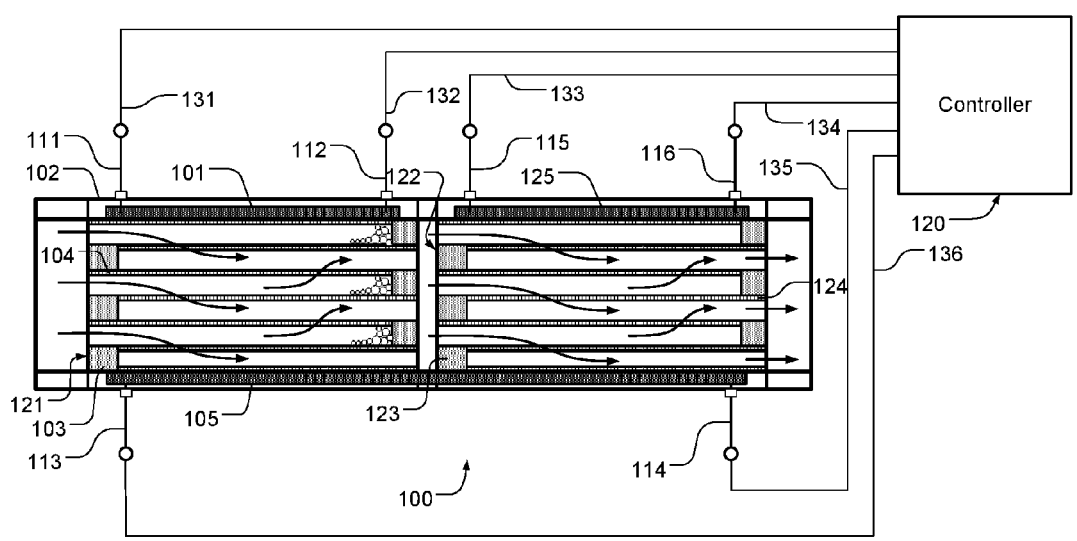
FIG. 1a is a schematic representation of a PM sensing device including sensing pieces and a sensor controller.

Referring to FIG. 1a, an exemplary PM sensor includes a sensing unit 100 and a controller 120. The sensing unit 100 has an outer housing 102, inside which a front particulate filter piece 121 and a back particulate filter piece 122 are enclosed. On top of the front particulate filter piece 121, an electrode 101 has two lead wires 111 and 112 electrically connected to the controller 120 through signal lines 131 and 132 respectively, while an electrode 125 is positioned on top of the back particulate filter piece 122 with two lead wires 115 and 116 electrically connected to the controller 120 through signal lines 133 and 134 respectively. The particulate filter pieces 121 and 122 are wall-flow particulate filters. In the front particulate filter piece 121, blocked by channel plugs 103, exhaust gas flows through channel walls 104 with PM trapped therein. The filtered exhaust gas then enters the back particulate filter piece 122. Blocked by channel plugs 123, the exhaust gas goes through its channel walls 124. Under the front particulate filter piece 121 and the back particulate filter piece 122, an electrode 105 has two lead wires 113 and 114 electrically connected to the controller 120 through signal lines 136 and 135 respectively.

The electrodes 101 and 105, and the electrodes 125 and 105 form two capacitive sensors, while the resistance of the electrode 101 in between the two lead wires 111 and 112, and that of the electrode 125 in between the two lead wires 115 and 116 change with temperature. The electrode 105 is used as a resistive heater when a current is applied through the lead wires 113 and 114, and the resistance of the electrode 105 in between the two lead wires 113 and 114 also changes with temperature.

Figure 1B:
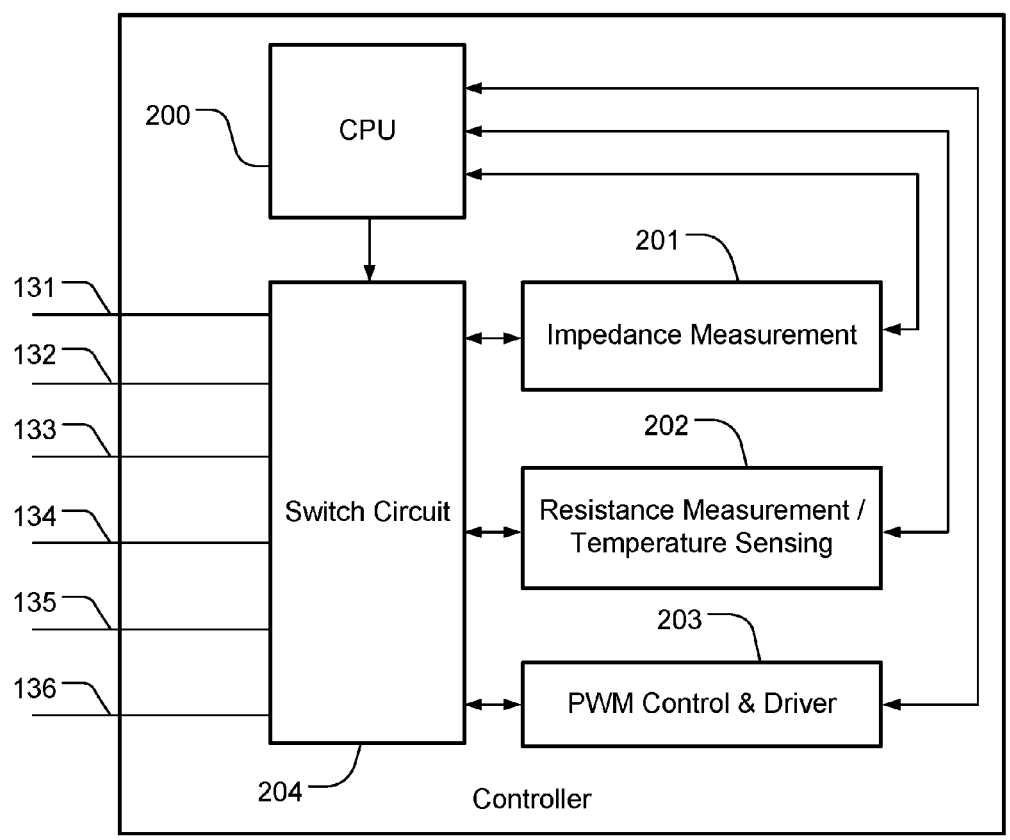
FIG. 1b is a block diagram of a sensor controller.

With the electrodes 101, 125, and 105, different functions and configurations can be achieved in the controller 120. An embodiment of the controller 120 is depicted in FIG. 1b. In the controller 120, the signal lines 131, 132, 133, 134, 135, and 136 are connected to a switch circuit 204 which is controlled by a CPU 200 including a microprocessor, a program memory, a data memory, and an interface circuit (not shown). The CPU 200 also controls an impedance measurement unit 201, a resistance measurement and temperature sensing unit 202, and a PWM control and driver unit 203. The units 201, 202 and 203 are connected to the switch circuit 204, which further connects different signal lines thereto under different configurations.

Figure 2A:
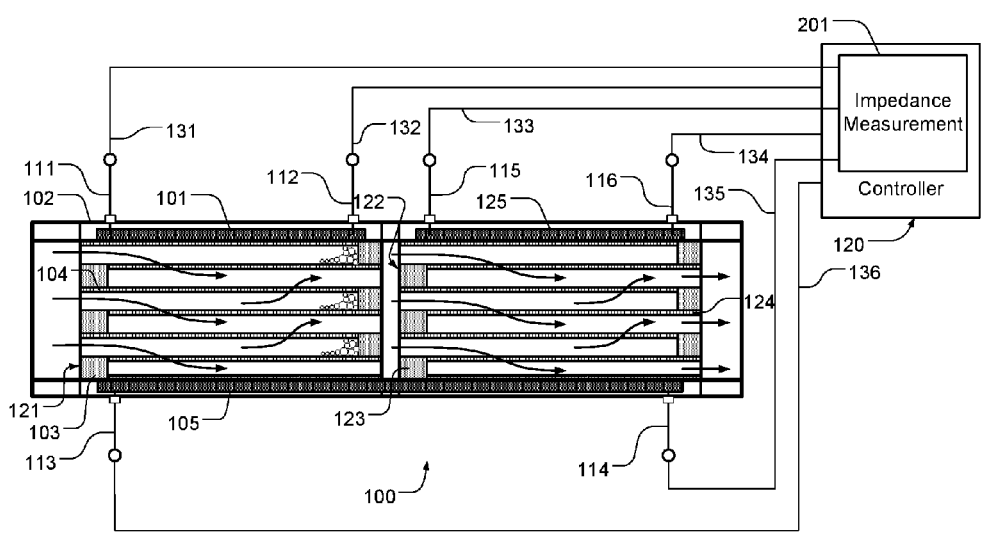
FIG. 2a is a schematic representation of a PM sensing device with its sensor controller set to an impedance measurement mode.
Figure 3A:
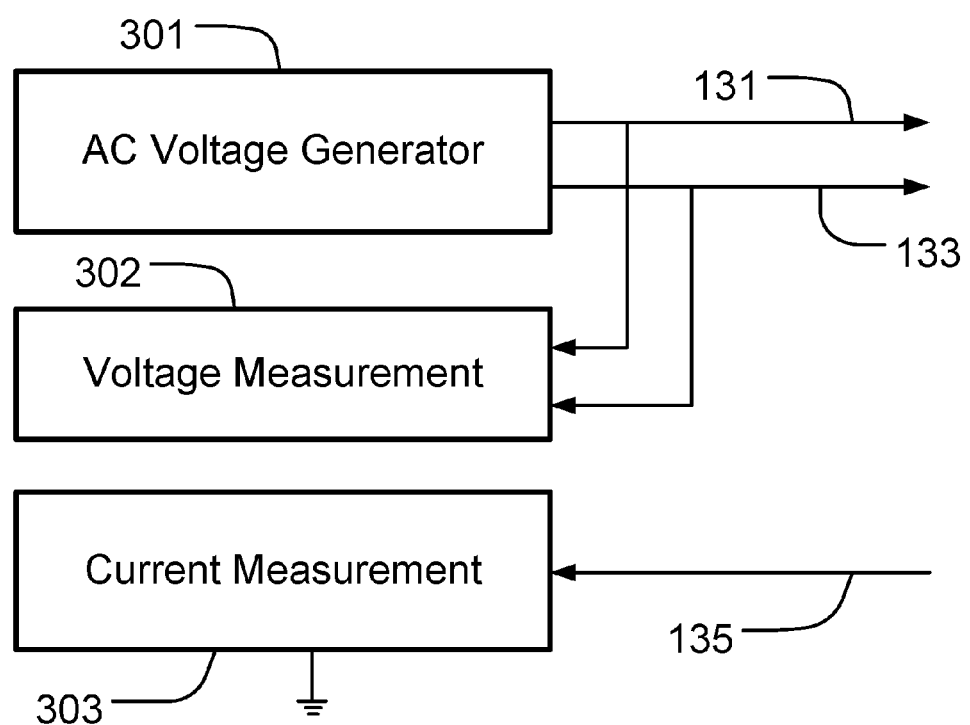
FIG. 3a is a block diagram showing functional blocks in a sensor controller when it is set to an impedance measurement mode.

When the electrodes 101, 125, and 105 are configured as capacitive sensors, the impedance measurement unit 201 is connected to lead wires 111, 115, and 114 through the signal lines 131, 133, and 135, as shown in FIG. 2a. In the impedance measurement unit 201, the impedance between the electrodes 101 and 105, and the impedance between the electrodes 125 and 105 are measured. A variety of methods can be used for measuring impedance. In an exemplary circuit, as depicted in FIG. 3a, an AC voltage generator 301, which generates a sinuous signal or a pulse signal, and applies this signal to the lead wires 111 and 115 through the signal lines 131 and 133. The voltages on the signal lines 131 and 133 are measured through a voltage measurement circuit 302, and the current on the signal line 135, which is connected to the lead wire 114, is measured through a current measurement circuit 303. With the measured voltages and the current, the impedance between the electrodes 101 and 105, and that between the electrodes 125 and 105, can be calculated.

Figure 2B:
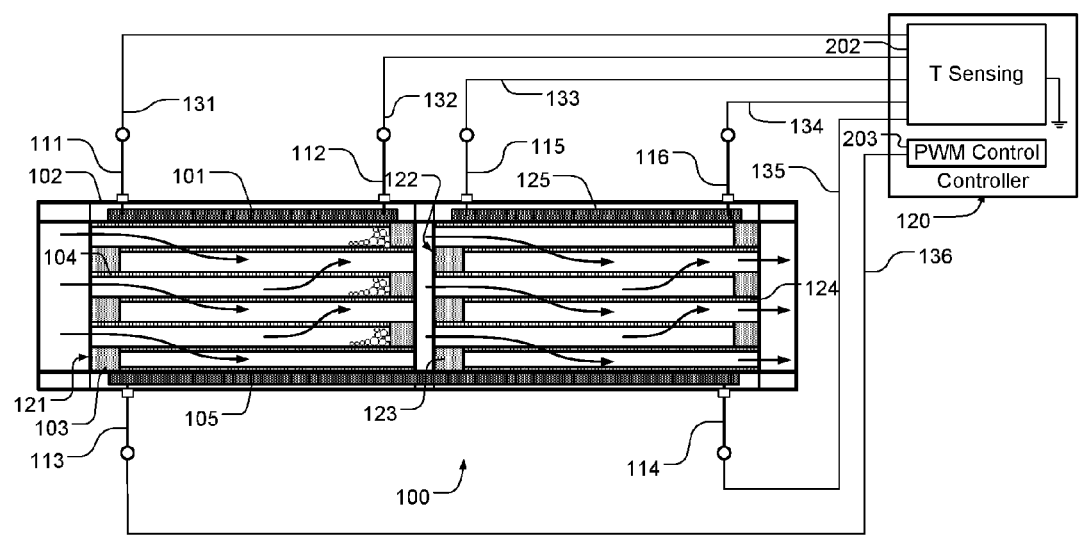
FIG. 2b is a schematic representation of a PM sensing device with its sensor controller set to a regeneration mode.
Figure 3B:
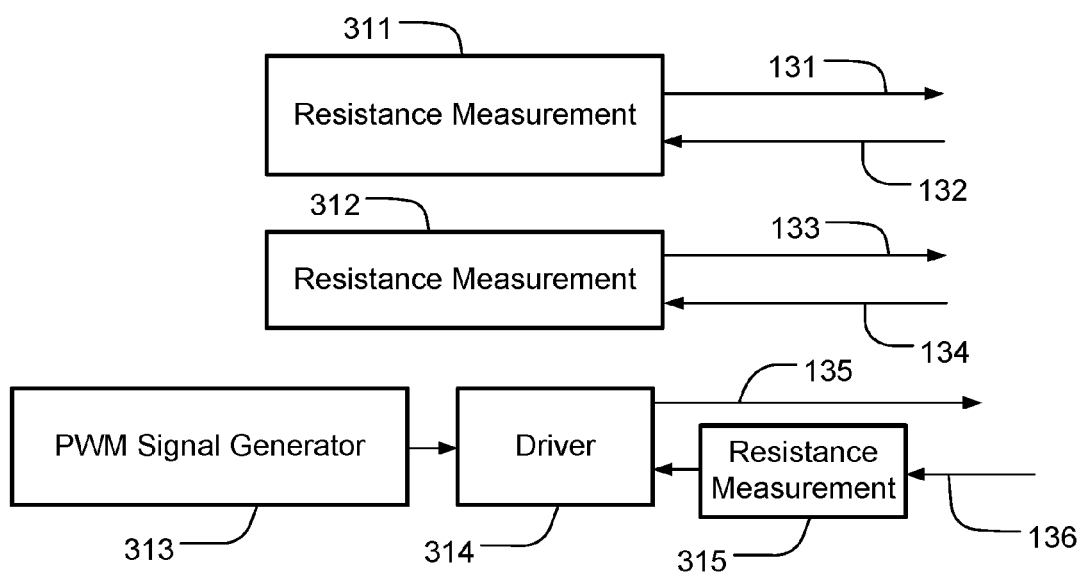
FIG. 3b is a block diagram showing functional blocks in a sensor controller when it is set to a regeneration mode.

When PM is accumulated to a certain level in the front particulate filter piece 121, a regeneration process for the sensor is triggered. In the regeneration process, a PWM signal is applied on the lead wires 113 and 114 of the electrode 105 to resistively heat the electrode 105, and the temperature of the sensor is detected by measuring the resistance between the lead wires 111 and 112 of the electrode 101, the resistance between the lead wires 113 and 114 of the electrode 105, and that between the lead wires 115 and 116 of the electrode 125. Such a configuration is shown in FIG. 2b, in which the temperature sensing unit 202 is electrically connected to lead wires 111, 112, 115, and 116 through the signal lines 131, 132, 133, and 134 respectively, while the PWM control unit is electrically connected to the lead wire 113 through the signal lines 136. The lead wire 114 is grounded through the signal lines 135. A variety of methods can be used in measuring the resistance and generating the PWM control signal. As shown in FIG. 3b, in an exemplary circuit, a resistance measurement circuit 311 is electrically connected to the lead wires 111 and 112 through the signal lines 131 and 132 respectively for measuring a resistance of the electrode 101, while a resistance of the electrode 125 is measured by a resistance measurement circuit 312, which is electrically connected to the lead wires 115 and 116 through the signal lines 133 and 134. A PWM signal generator 313 is used for generating a PWM signal, which is applied to the electrodes 105 through a driver circuit 314 electrically connected to signal lines 135. And through a resistance measurement circuit 315, which is connected in between the signal lines 136 and the driver circuit 314, a resistance between the lead wires 113 and 114 is measured.

When PM accumulates inside the front particulate filter piece 121 and the back particulate filter piece 122, the capacitance between the electrodes 101 and 105, and between the electrodes 125 and 105 increase, since the accumulated PM equivalently decreases the distance between the two electrodes. Additionally, the capacitance also varies with exhaust gas temperature and exhaust gas species, due to a change in dielectric constant.

In the sensor of FIG. 1a, when exhaust gas flows through its inlet to its outlet, i.e., when the sensor 100 is positioned in an exhaust flow with its inlet receiving exhaust gas, since the front particulate filter piece 121 is upstream from the back particulate filter piece 122, PM accumulates in the front particulate filter piece 121 and only filtered exhaust gas passes through the back particulate filter piece 122. As a result, PM in the sensor only affects the capacitance between the electrodes 101 and 105, and PM deposit amount in the sensor 100 can be detected by comparing the capacitance between the electrodes 101 and 105, Cf, and that between the electrodes 125 and 105, Cb.

A variety of methods can be used in calculating a parameter indicative of a PM deposit amount in the senor 100 by comparing the Cf and Cb values. In an exemplary method, a ratio of Cf to Cb, Rp, is obtained by calculating a ratio of an impedance between the electrodes 125 and 105, Zb, to an impedance between the electrodes 101 and 105, Zf:

$$Rp = Zb/Zf = Cf/Cb \qquad (1).$$

Figure 4A:
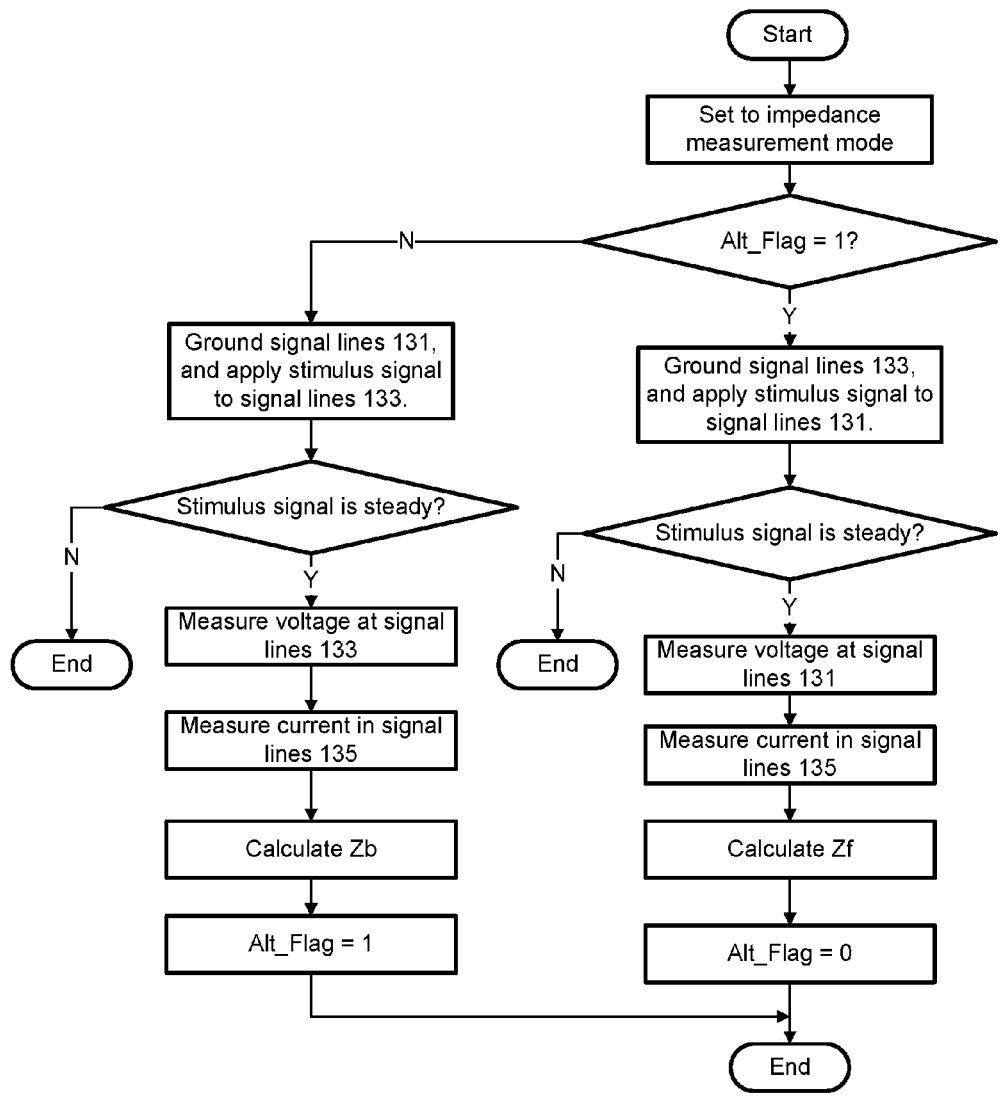
FIG. 4a is a flow chart of a service routine running periodically for a timer based interrupt for calculating impedances in a PM sensor.

The Zb and Zf values can be measured by applying sinuous or pulse signals to the signal lines 131 and 133 alternately and measuring current passing through the signal lines 135, with an impedance measurement unit 201 as depicted in FIG. 3a. A service routine running periodically in the CPU 200 for a timer-based interrupt can be used for the impedance measurement, as shown in FIG. 4a. In this routine, at the beginning, the controller 120 is set to an impedance measurement mode, in which the impedance measurement unit 201 is electrically connected to the signal lines 131, 133, and 114. Then a flag Alt_Flag is examined. If the flag value is zero, then the signal lines 131 are grounded and a stimulus signal is applied to the signal lines 133. After the stimulus signal is steady, a voltage at the signal lines 133 and a current in the signal lines 135 are measured. With the voltage and current, the Zb value is calculated. The routine ends after the flag Alt_Flag is set to one. Referring back to the examination of the Alt_Flag value, if it is one, then the signal lines 133 are grounded, and a stimulus signal is applied to the signal lines 131. After the stimulus signal is ready, a voltage at the signal lines 131 and a current in the signal lines 135 are measured, and the Zf value is calculated thereafter. Then the Alt_Flag value is reset to zero, and the routine ends.

Figure 4B:
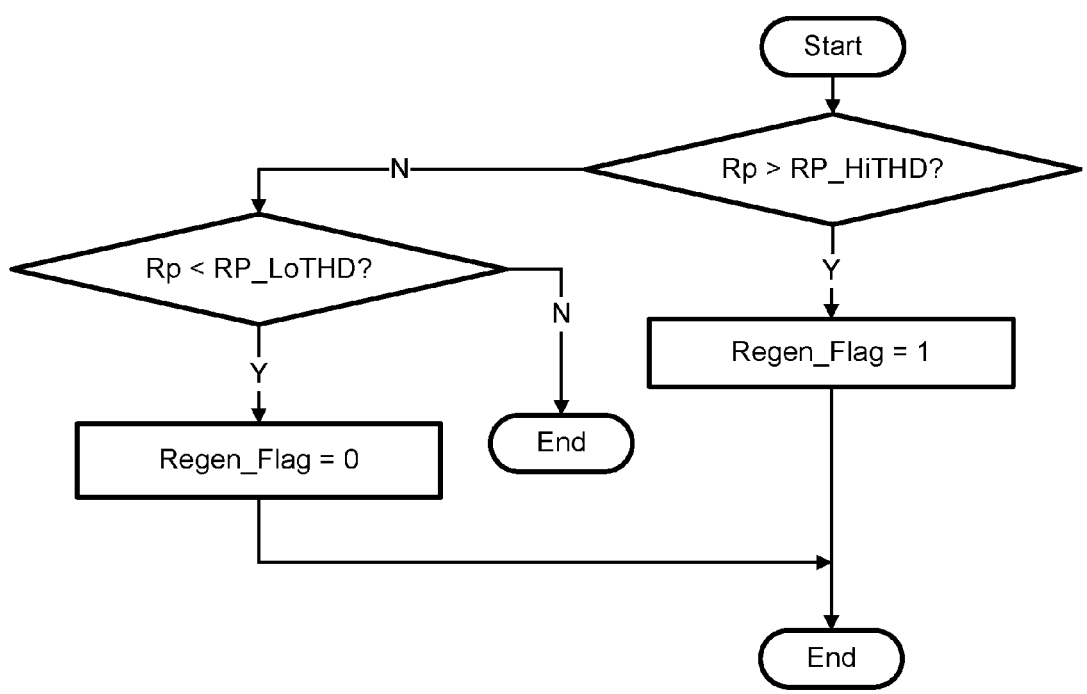
FIG. 4b is a flow chart of a service routine running periodically for a timer based interrupt for triggering sensor regeneration processes.

When PM accumulates in the sensor 100 to a certain level, a regeneration process is needed to remove the accumulated PM. Such a regeneration process can be achieved by heating the front articulate filter piece 121 and the back particulate filter piece 122 above a regeneration temperature at which PM starts to effectively react with oxygen. With the Rp value calculated with the Zb and Zf values, a PM accumulation level in the front particulate filter piece 121 can be detected, and thereby, the regeneration process can be triggered and terminated with the Rp values. A simple algorithm for triggering and terminating a regeneration process can be realized with a routine shown in FIG. 4b. In this routine, after it starts, the Rp value is compared with a threshold RP_HiTHD. If the Rp value is higher than this threshold, then a flag Regen_Flag, is set to one, upon which a sensor regeneration is triggered, otherwise, if the Rp value is lower than another threshold RP_LoTHD, then the flag Regen_Flag is reset to zero, with which a sensor regeneration is terminated. If the Rp value is in between the two thresholds RP_LoTHD, and the flag Rgen_Flag keeps its previous value. The routine ends thereafter.

Figure 4C:
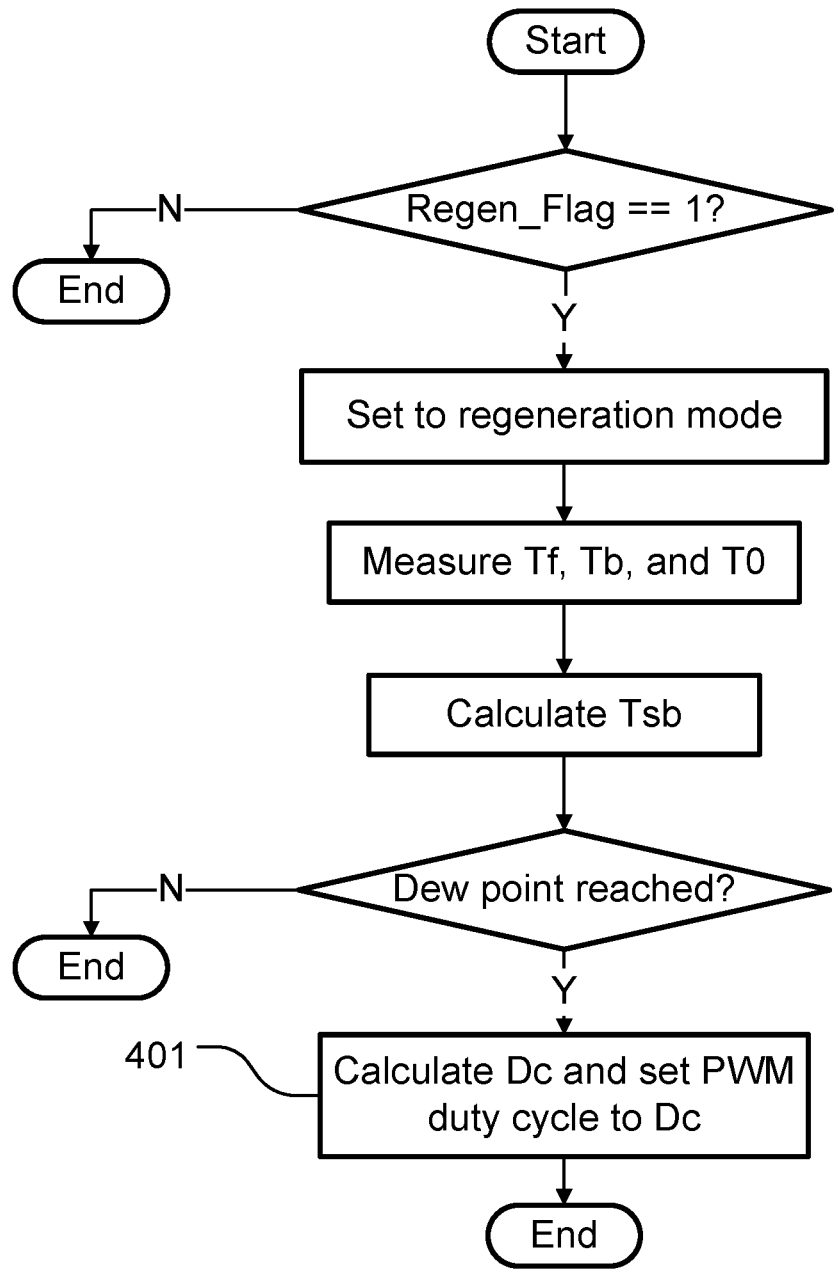
FIG. 4c is a flow chart of a service routine running periodically for a timer based interrupt for controlling sensor heating with dew point detection.

In a regeneration process of the sensor 100, sensor temperature can be controlled in closed-loop with a service routine running periodically for a timer based interrupt. Referring to FIG. 4c, in such a routine, the flag Regen_flag is examined right after the routine starts. The routine ends if the Regen_Flag value is not one, otherwise, the controller 120 is set to a regeneration mode, in which the PWM control unit 203 is connected to the signal lines 136, while the signal lines 135 are connected to a ground through the temperature sensing unit 202 (FIG. 2b). In the regeneration mode, a PWM signal with a duty cycle Dc is applied on the signal lines 136. And the minimum value of Dc is set to above zero for measuring the resistance in between the lead wires 113 and 114. In the routine, after the controller 120 is configured to the regeneration mode, a resistance between the lead wires 111 and 112, Rf, a resistance between the lead wires 115 and 116, Rb, and a resistance between the lead wires 113 and 114, R0, are measured, and a temperature of the electrode 110, Tf, a temperature of the electrode 125, Tb, and a temperature of the electrode 105, T0, are calculated with the Rf, Rb, and R0 values. The temperatures of the electrodes are then used for calculating a bed temperature of the sensor 100, Tsb. With different definitions, different methods can be used for calculating the bed temperature Tsb. In a simple method, the Tsb value can be calculated with the following equation:

$$Tsb=[(Tf+Tb)/2+T0]/2 \qquad (2).$$

After the Tsb value is obtained, it is compared to a dew point value, e.g., 100° C. The dew point examination is to avoid damage to the sensor caused by condensed moisture on the electrodes 101, 125, and 105 when the sensor 100 is regenerated. The dew point is deemed to be reached after the Tsb value is above the dew point value for a certain time, e.g., 120s. If the dew point is not reached, then the routine ends after the dew point examination, otherwise, in a step 401, the duty cycle Dc is calculated and sent to the PWM control unit 203, where a PWM signal with the duty cycle setting of Dc is generated. The routine ends thereafter.

Figure 4D:
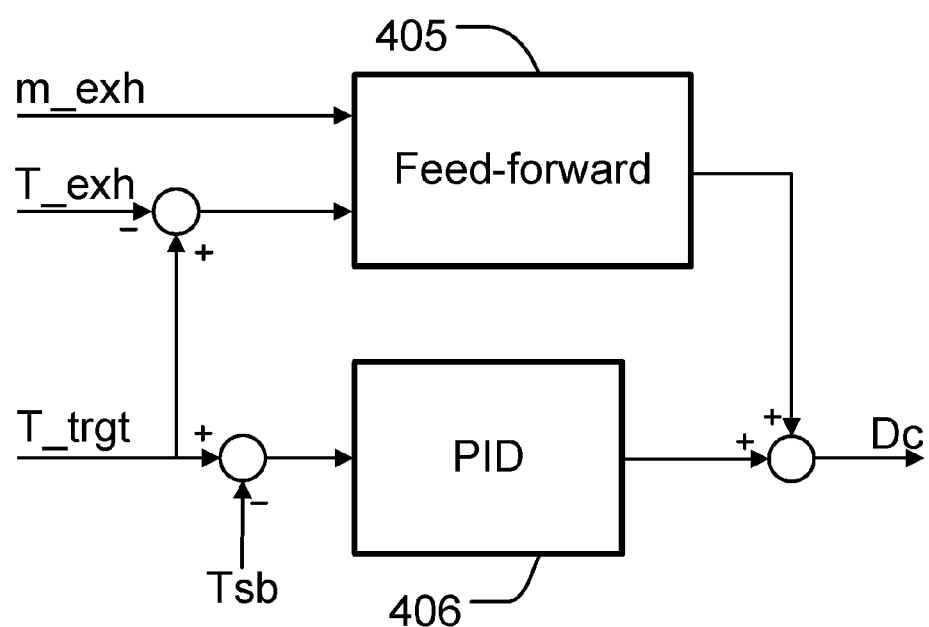
FIG. 4d is a block diagram of a temperature control loop for sensor heating control in regenerating a PM sensor.

In the step 401 of the service routine, the duty cycle Dc can be calculated in a closed-loop control. Referring to FIG. 4*d*, in an exemplary closed loop control, a feed-forward block 405 is used for calculating a base-line for the Dc value with two inputs of an exhaust mass flow rate m_exh, and a difference between a target regeneration-temperature command T_trgt and an exhaust gas temperature T_exh. In the feed-forward block 405, a simple lookup table with two inputs of the m_exh value and the temperature difference value can be used in calculating the base-line value, and the lookup table can be populated using testing results with different exhaust flow rate, target regeneration-temperature, and exhaust temperature settings. The m_exh and T_exh values in the closed loop control can be obtained from an ECU (Engine Control Unit, not shown) through communication. In the closed-loop control, the T_trgt value also compares with the calculated Tsb value. The difference between the T_trgt value and the Tsb value is used in a PID control block 406 for calculating a correction value, which is then added to the base-line value calculated in the feed-forward block 405, resulting in the Dc value. With the closed-loop control, the bed temperature of the sensor 100 can be controlled at the T_trgt value, which is set to be higher than a light-off temperature, above which PM can be oxidized effectively by oxygen.

In a DPF system, the sensor 100 can be positioned upstream or downstream from a DPF. In an embodiment, referring to FIG. 5*a* and FIG. 5*b*, a DPF system includes a wall-flow DPF 502 positioned downstream from a heating device 501, which is used for heating exhaust gas when regenerating the DPF 502. The sensor 100 can be positioned upstream from the heating device 501 (FIG. 5*a*) or in between the heating device 501 and the DPF 502 (FIG. 5*b*). In these configurations, exhaust flow passes the sensor 100 before it goes through the DPF 502. A regeneration frequency, i.e., regeneration times in a predetermined period of time or a duration time between two regeneration processes is an indication of PM concentration in an exhaust flow passing through the sensor 100. This PM concentration information can be used in estimating PM loading in the DPF 502 and diagnosing issues in an engine.

Figure 6:
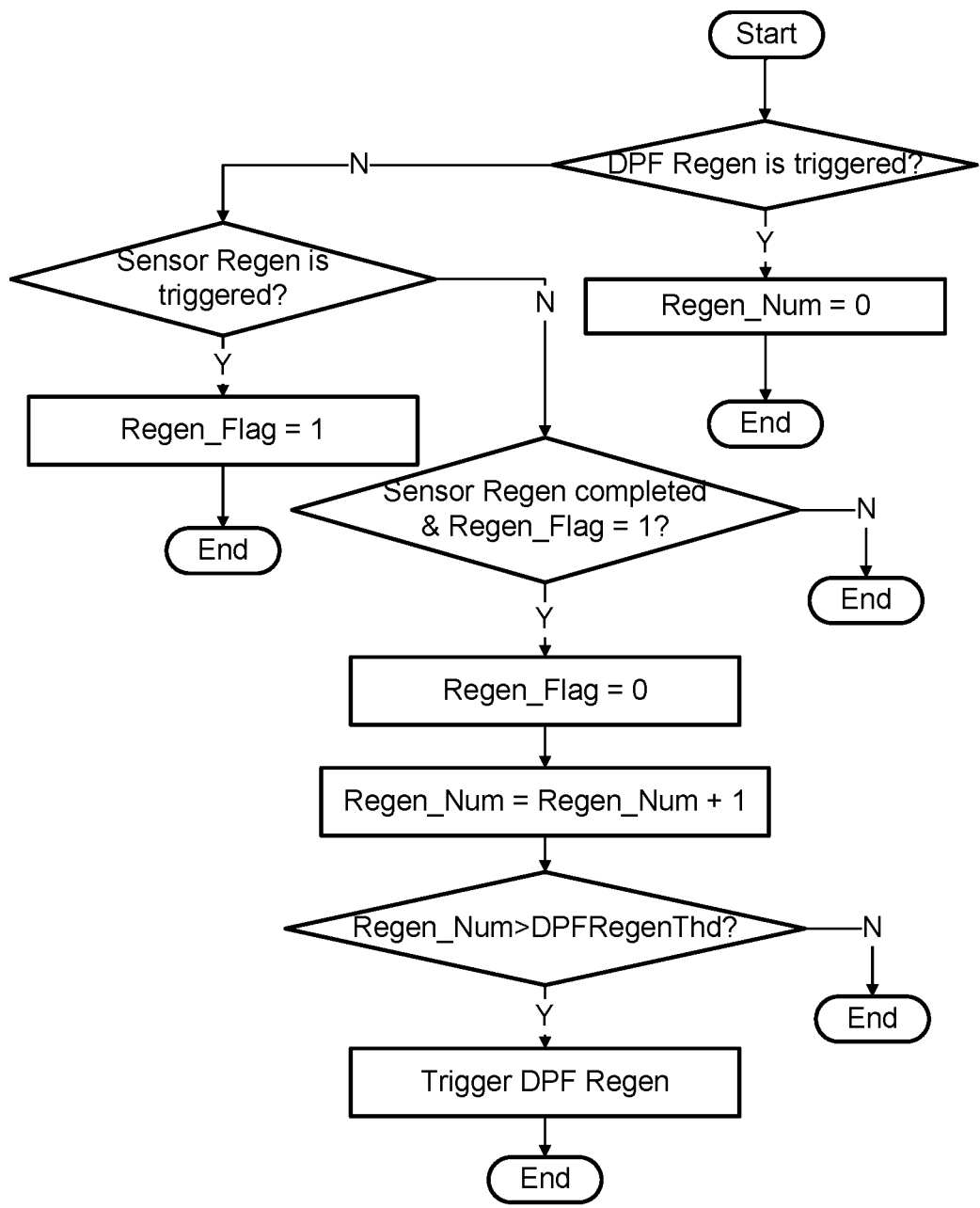
FIG. 6 is a flow chart of a service routine running periodically for a timer based interrupt for triggering a DPF regeneration.

Regeneration times of the sensor 100 can also be used directly to trigger regenerations of the DPF 502. Referring back to FIG. 1*a*, the sensor 100 has particulate filter pieces, which has the same wall-flow particulate filter structure as that of the DPF 502. In an exhaust flow, uniformly distributed PM makes the PM loading rate in the front DPF sensing piece an indication of the PM loading rate in the DPF 502, while regeneration times of the sensor 100 reflect a total amount of PM loaded therein. Accordingly, regeneration times of the sensor 100 are also indicative of a total amount of PM loaded in the DPF 502. Referring to FIG. 6, a service routine running periodically for a timer-based interrupt can be used for triggering DPF regenerations with sensor regeneration times. In this routine, a DPF regeneration status is firstly checked. If a DPF regeneration is triggered, then a variable Regen_Num is reset to zero and the routine ends, otherwise, a sensor regeneration status is checked. If a sensor regeneration is triggered, then a flag Regen_Flag is set to one, and the routine ends, otherwise, the routine ends if the sensor is still in regeneration or the Regen_Flag value is not one. If a sensor regeneration is completed and the Regen_Flag value is one, then the flag Regen_Flag is reset to zero, and the Regen_Num value is incremented by one. The incremented Regen_Num value is then compared with a threshold DPFRegenThd. The routine ends if it is not higher than the threshold value, otherwise, a DPF regeneration is triggered and the routine ends thereafter.

The PM sensor can also be used for diagnosing engine issues. In this application, a PM ratio, which is a ratio of the regeneration times during a predetermined time period to a fuel amount burned in an engine in the predetermined time period, is compared to an expected value determined by operating status of the engine. A sudden change of the difference between the PM ratio value and the expected value is an indication of engine issues. The fuel amount in calculating the PM ratio value can be obtained by integrating a fueling rate obtained from an ECU or calculated with lambda values or O2 concentration values measured using a lambda sensor and an exhaust mass flow-rate.

Figure 5A:
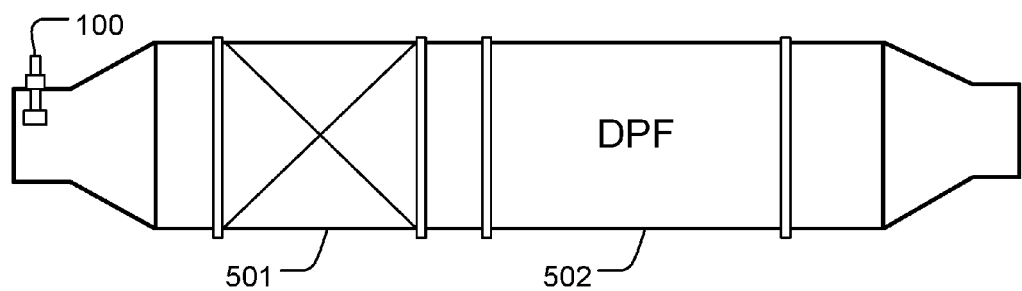
FIG. 5a is a schematic representation of a DPF system with a PM sensor positioned upstream from a heating device.
Figure 5B:
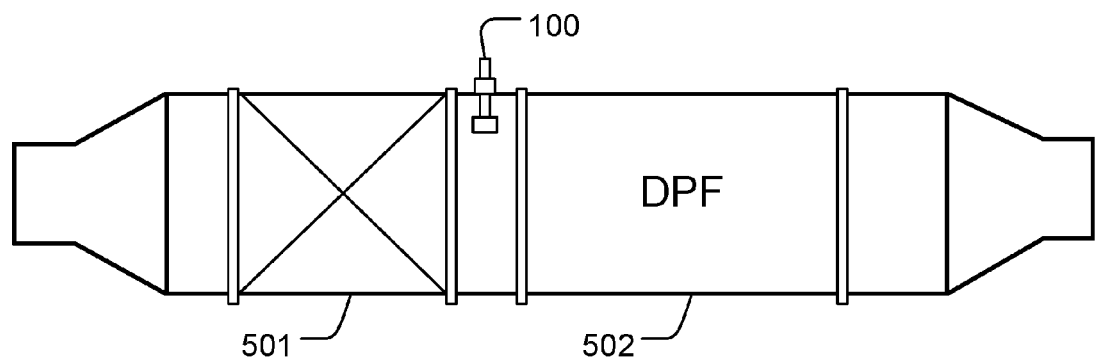
FIG. 5b is a schematic representation of a DPF system with a PM sensor positioned in between a heating device and a DPF.

In the system of FIG. 5*a*, a variety of devices can be used in the heating device 501, including but not limited to fuel burners, DOCs (Diesel Oxidation Catalyst), and electrical heaters. If a DOC is used in the heating device 501, since PM, especially SOF (Soluble Organic Fraction), can be burned in a DOC, an uncertainty could be introduced when the sensor 100 is positioned in between the heating device 501 and the DPF 502 as shown in FIG. 5*b*, and used in measuring engine PM emission, or when it is positioned upstream from the heating device 501, and used in triggering DPF regenerations. This amount of PM burned in DOC can be compensated to make sensing values obtained from the sensor 100 more accurate, and a simple compensation method can be calculating a compensation factor, which is a function of an average exhaust gas temperature, and multiplying the compensation factor with a sensor regeneration frequency or an interval time between two sensor regeneration processes.

Figure 5C:
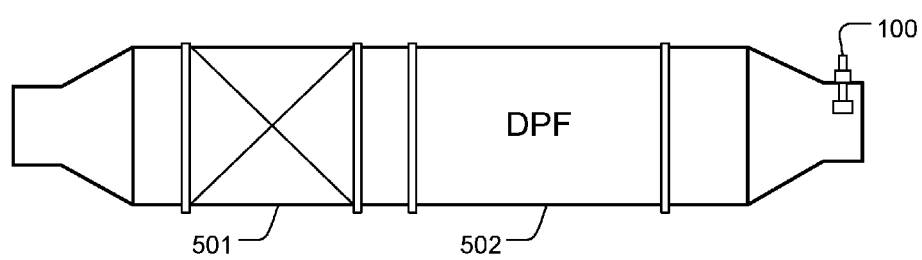
FIG. 5c is a schematic representation of a DPF system with a PM sensor positioned downstream from a DPF.
Figure 7A:
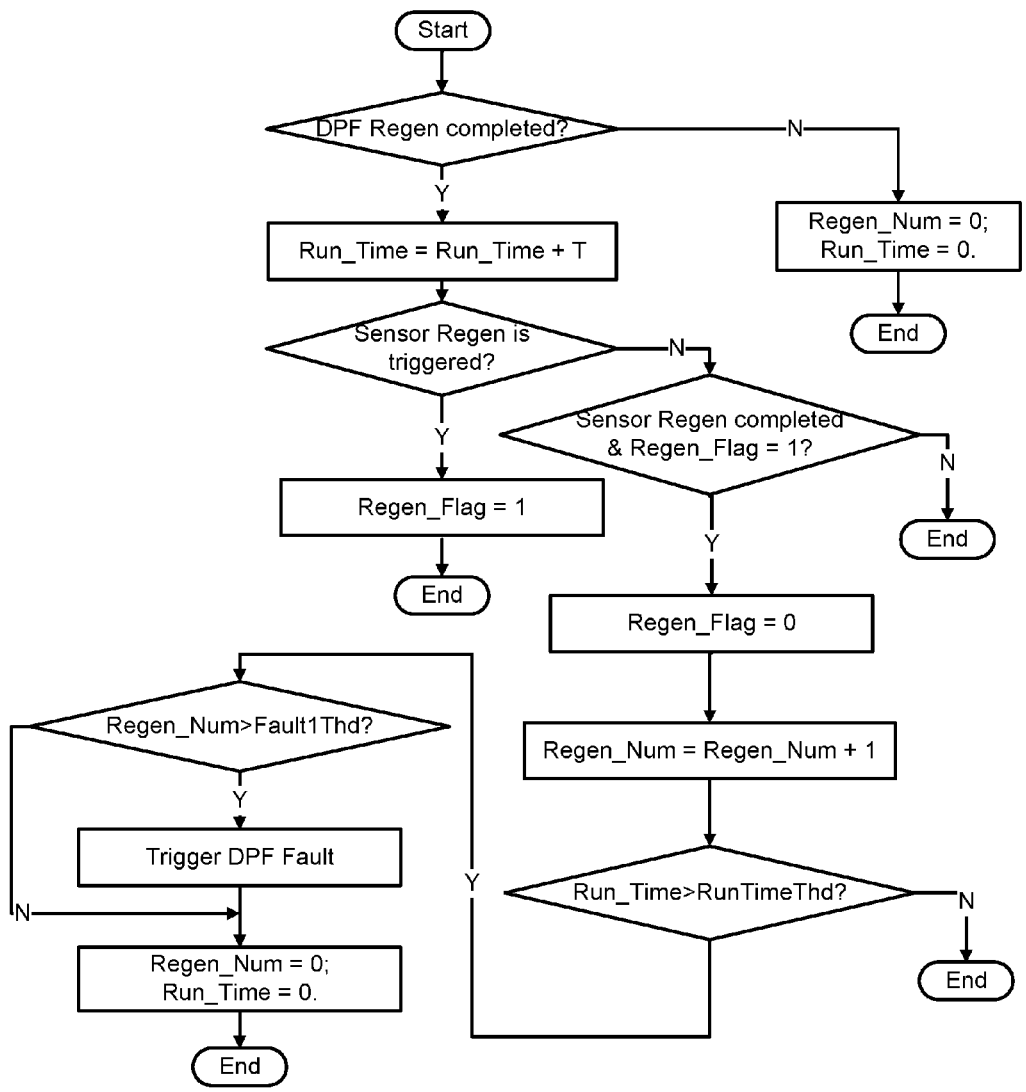
FIG. 7a is a flow chart of a service routine running periodically for a timer based interrupt for detecting a DPF system failure with a sensor regeneration number value.

In addition to positioning the sensor 100 upstream from the DPF 502, the sensor 100 can also be positioned downstream from the DPF 502, as shown in FIG. 5*c*. In such a configuration, the sensor 100 can be used for diagnosing issues in the DPF system. And a diagnostic algorithm can be realized with a service routine running periodically for a timer-based interrupt. Referring to FIG. 7*a*, in such a routine, when it starts, a DPF regeneration status is examined. If a DPF regeneration is not completed, then variables Regen_Num and Run_Time are reset to zero, and the routine ends. Otherwise, the Run_Time value is incremented by a number T, which is the interval time of the timer-based interrupt. A sensor regeneration status is checked thereafter. If a sensor regeneration is triggered, then the Regen_Flag is set to one and the routine ends. If a sensor regeneration is not completed or the Regen_Flag value is not one, then the routine ends, otherwise, the Regen_Flag value is set to zero and the Regen_Num is incremented by one. The Run_Time value is then compared with a threshold RunTimeThd, and the routine ends if it is not higher than the threshold. If it is higher than the threshold, then the Regen_Num is further compared with a threshold Fault1Thd, and a DPF fault is triggered when the Regen_Num value is higher than the threshold Fault1Thd. The routine ends after the Regen_Num and the Run_Time values are reset to zero. In this algorithm, the DPF fault indicates a DPF system failure due to a significant decrease of filter efficiency or a significant increase of engine emission.

Figure 7B:
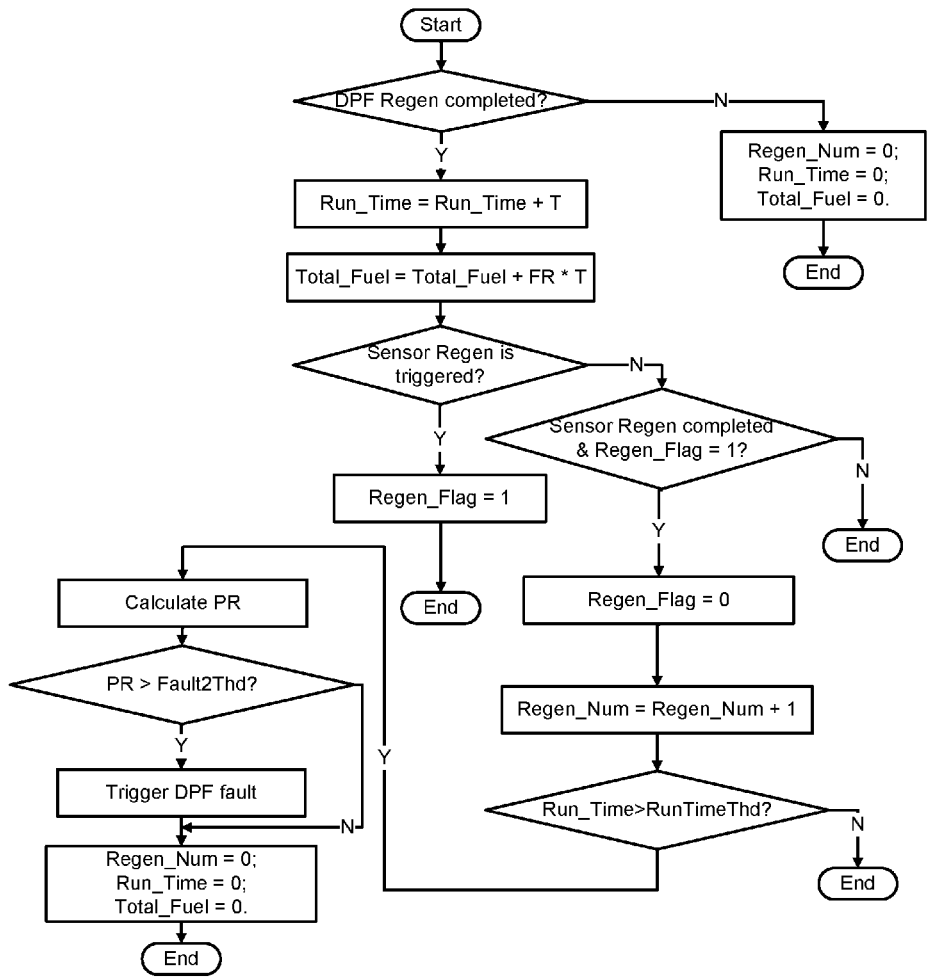
FIG. 7b is a flow chart of a service routine running periodically for a timer based interrupt for detecting a DPF system failure with a PM ratio value.

In detecting DPF system failures, high engine PM emission sometimes also increases PM concentration downstream from the DPF. To avoid false alarms caused by engine operating modes with high PM emission, a PM ratio value can be calculated and used for triggering DPF faults. Referring to FIG. 7b, a service routine similar to that of FIG. 7a can be used in calculating the PM ratio value and triggering DPF faults. In this routine, in addition to the Regne_Time and the Regen_Num values, a fueling amount value, Total_Fuel, and a PM ratio value, PR, are also calculated. The Total_Fuel value is calculated with a fueling rate, FR, which can be either obtained from an ECU or calculated with lambda values or O2 concentration values measured using a lambda sensor and an exhaust mass flow-rate. And the PR value can be calculated with the following equation:

$$PR=Regen\_Num/Total\_Fuel \quad (3).$$

If the calculated PR value is higher than a threshold Fault2Thd, then a DPF system fault is triggered.

Figure 5D:
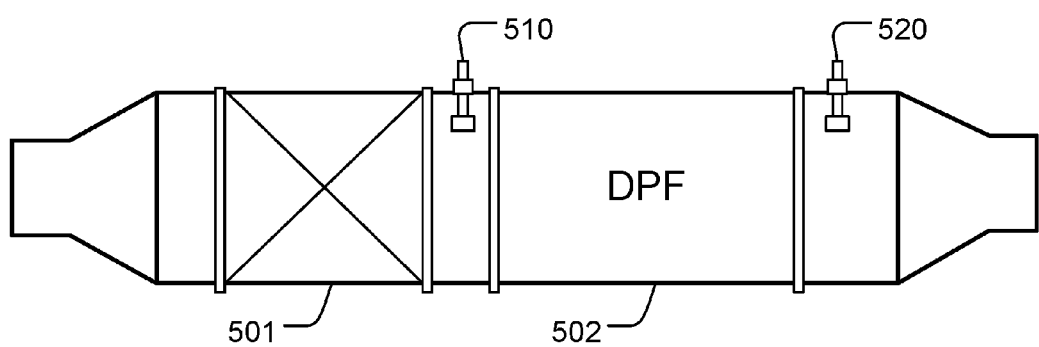
FIG. 5d is a schematic representation of a DPF system with a first PM sensor positioned upstream from a DPF and a second PM sensor positioned downstream from a DPF.

In addition to DPF system failures, DPF component failures can also be detected. Referring to FIG. 5d, in a DPF system, a sensor 510 positioned in between the heating device 501 and the DPF 502 together with a sensor 520 installed downstream from the DPF 502 are used in detecting issues in the DPF 502. The sensors 510 and 520 are the same type as the senor 100.

Figure 8:
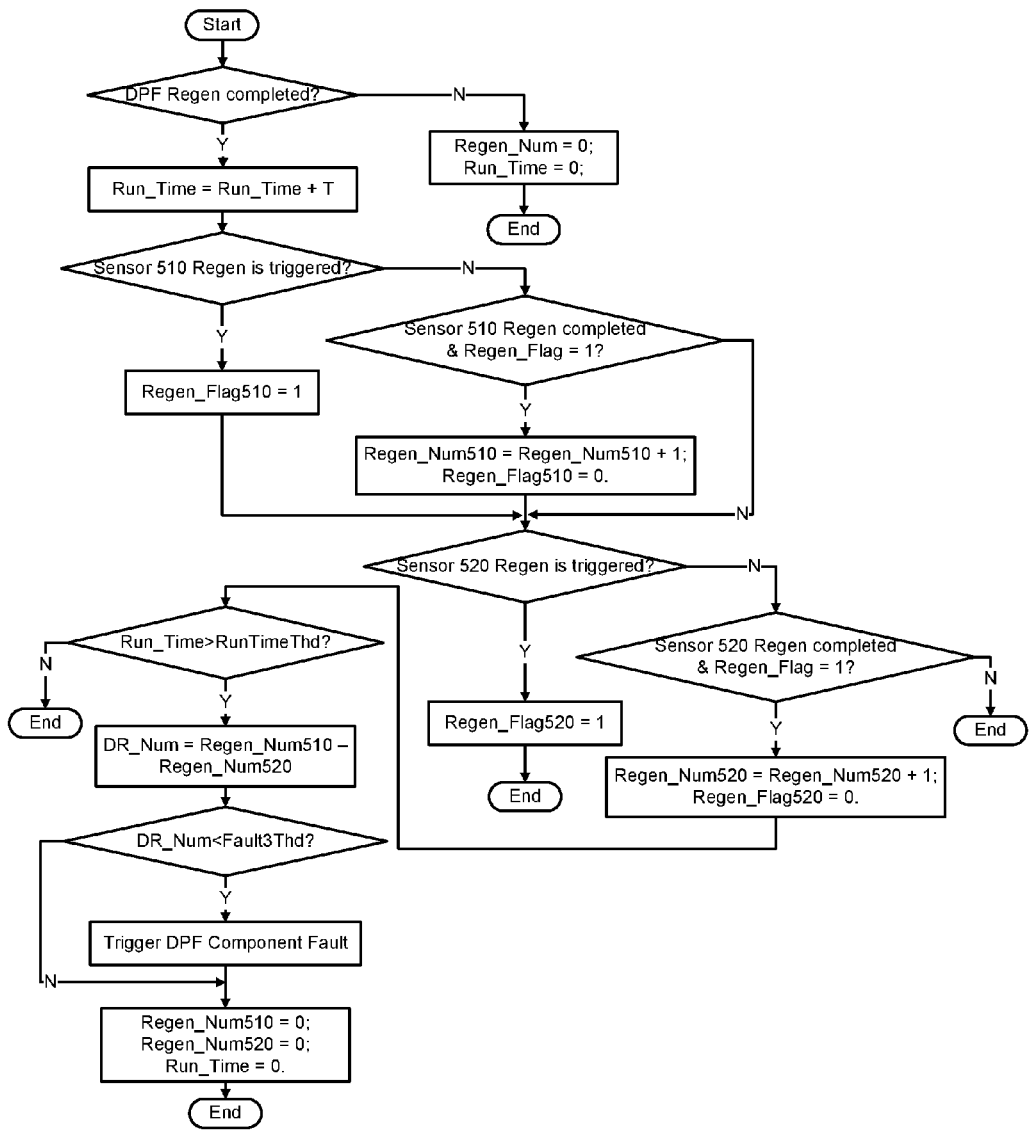
FIG. 8 is a flow chart of a service routine running periodically for a timer based interrupt for detecting a DPF device failure.

An exemplary algorithm for the failure detection can be realized with a service routine running periodically for a timer based interrupt. Referring to FIG. 8, in such a routine, both of regeneration times of the sensor 510, Regen_Num510, and that of the sensor 520, Regen_Num520, are calculated in a time period Run_Time. And a difference between the regeneration times, DR_Num, is calculated thereafter. If the DR_Num value, which is an indication of a filter efficiency of the DPF 502, is lower than a threshold Fault3Thd, then a DPF component fault is triggered.

The exemplary service routines in FIGS. 7a, 7b, and 8 have only processes of setting faults with a first limit threshold. To clear faults, a second limit threshold can be used. For example, in the service routine of FIG. 7a, a second limit threshold, Clear1Thd, can be compared to the Regen_Num value when the Run_Time value is higher than the threshold RegenTimeThd and before it is compared to the threshold Fault1Thd. If the threshold Clear1Thd is higher than the Regne_Num value, then the DPF fault can be cleared. The service routines with fault setting and fault clearing can be further used in OBD applications.

Referring back to FIGS. 2a, 2b, 4a, and 4b, when a PWM signal is applied to the electrode 105, temperatures measured with the electrodes 105, 102, and 125 should increase, and the Rp value should decrease. Accordingly, after a predetermined period of time, the temperatures reach above a certain value or the Rp value drop below a certain values. If the high temperatures and low Rp value are not obtained, then the sensor 100 fails. The changes in the electrode temperatures and the Rp value in a period of time after a sensor regeneration starts can be used for diagnosing sensor rationality issues.

While the present invention has been depicted and described with reference to only a limited number of particular preferred embodiments, as will be understood by those of skill in the art, changes, modifications, and equivalents in form and function may be made to the invention without departing from the essential characteristics thereof. Accordingly, the invention is intended to be only limited by the spirit and scope as defined in the appended claims, giving full cognizance to equivalents in all respects.

The invention claimed is:

1. A sensing device for detecting particulate matters in an exhaust gas processing system of an internal combustion engine, comprising:
   a first particulate filter piece positioned in between a first electrode and a second electrode receiving an incoming exhaust gas flow;
   a second particulate filter piece positioned in between a third electrode and said second electrode receiving an exhaust gas flow which passes through said first particulate filter piece;
   an impedance measurement circuit electrically connected to said first electrode, said second electrode and said third electrode, generating a first impedance sensing signal indicative of an impedance in between said first electrode and said second electrode and a second impedance sensing signal indicative of an impedance in between said third electrode and said second electrode; and
   a controller adapted to provide a PM sensing signal indicative of a particulate matters amount in said incoming exhaust gas flow in response to said first impedance sensing signal and said second impedance sensing signal.

2. The sensing device of claim 1, wherein said controller is further configured to calculate a ratio of said impedance in between said first electrode and said second electrode to said impedance in between said third electrode and said second electrode in response to said first impedance sensing signal and said second impedance sensing signal, and generate said PM sensing signal in response to said ratio.

3. The sensing device of claim 1, further comprising:
   a resistive heating circuit electrically connected to said second electrode, wherein said controller is further configured to generate a control signal and apply said control signal to said second electrode through said resistive heating circuit.

4. The sensing device of claim 3, wherein said control signal is a PWM signal.

5. The sensing device of claim 3, wherein said controller is further configured to start a sensor regeneration process, in which said second electrode is resistively heated, in response to said PM sensing signal.

6. The sensing device of claim 5, wherein said controller is further configured to stop said sensor regeneration process in response to said PM sensing signal.

7. The sensing device of claim 5, wherein said controller is further configured to start said sensor regeneration process when a temperature of said incoming exhaust gas flow passing through said first particulate filter piece is higher than a predetermined value.

8. The sensing device of claim 3, further comprising:
   a resistance measurement circuit generating a first sensing signal indicative of a resistance of said first electrode, a second sensing signal indicative of a resistance of said second electrode, and a third sensing signal indicative of resistance of said third electrode.

9. The sensing device of claim 8, wherein said controller is further configured to calculate a first temperature, a second temperature, and a third temperature, in response to said first sensing signal, said second sensing signal, and said third sensing signal generated by said resistance measurement circuit respectively.

10. The sensing device of claim 9, wherein said controller is further configured to control a temperature in said sensor within a predetermined range by adjusting said control signal in response to said first temperature, said second temperature, and said third temperature.

11. The sensing device of claim 10, wherein said controller is further configured to set said control signal to de-energize said second electrode when a temperature calculated in response to said first temperature, said second temperature, and said third temperature is lower than a predetermined threshold.

12. The sensing device of claim 10, wherein said controller is further configured to adjust said control signal in response to a mass flow rate of said incoming exhaust gas flow passing through said first particulate filter piece.

13. An exhaust gas processing system of an internal combustion engine, comprising:
   a diesel particulate filter;
   a heating device positioned upstream from said diesel particulate filter for regenerating said diesel particulate filter;
   a PM sensor including a first particulate filter piece positioned in between a first electrode and a second electrode receiving an incoming exhaust gas flow, a second particulate filter piece positioned in between a third electrode and said second electrode receiving an exhaust gas flow which passes through said first particulate filter piece, an impedance measurement circuit electrically connected to said first electrode, said second electrode and said third electrode, generating a first impedance sensing signal indicative of an impedance in between said first electrode and said second electrode and a second impedance sensing signal indicative of an impedance in between said third electrode and said second electrode, and a sensor controller adapted to provide a PM sensing signal indicative of a particulate matters amount in said incoming exhaust gas flow in response to said first impedance sensing signal and said second impedance sensing signal; and
   a filter regeneration controller for regenerating said diesel particulate filter by operating said heating device in response to at least said PM sensing signal generated from said PM sensor.

14. The exhaust gas processing system of claim 13, wherein said sensor controller is further configured to start a sensor regeneration process, in which said second electrode in said PM sensor is resistively heated for removing PM deposited in said PM sensor, in response to said PM sensing signal.

15. The exhaust gas processing system of claim 14, wherein said PM sensor is positioned upstream from said diesel particulate filter and said filter regeneration controller is further configured to start a DPF regeneration process for removing PM deposited in said diesel particulate filter in response to at least a number of regeneration times of said PM sensor in a predetermined period of time.

16. The exhaust gas processing system of claim 14, further comprising:
   a diagnostic controller configured to determine and indicate a PM emission issue in said exhaust gas processing system in response to at least a number of regeneration times of said PM sensor in a predetermined period of time.

17. A diagnostic control apparatus for detecting PM emission issues in an exhaust gas processing system of an internal combustion engine, comprising:
   a diesel particulate filter;
   a first PM sensor positioned downstream from said diesel particulate filter including a first particulate filter piece positioned in between a first electrode and a second electrode receiving an incoming exhaust gas flow, a second particulate filter piece positioned in between a third electrode and said second electrode receiving an exhaust gas flow which passes through said first particulate filter piece, an impedance measurement circuit electrically connected to said first electrode, said second electrode and said third electrode, generating a first impedance sensing signal indicative of an impedance in between said first electrode and said second electrode and a second impedance sensing signal indicative of an impedance in between said third electrode and said second electrode, and a sensor controller adapted to provide a first PM sensing signal indicative of a particulate matters amount in said incoming exhaust gas flow in response to said first impedance sensing signal and said second impedance sensing signal, and adapted to start a sensor regeneration process, in which said second electrode in said PM sensor is resistively heated for deposited PM, in response to said PM sensing signal; and
   a diagnostic controller configured to determine and indicate a PM emission issue in said exhaust gas processing system in response to at least said first PM sensing signal generated in said first PM sensor.

18. The diagnostic control apparatus of claim 17, wherein said diagnostic controller is further configured to determine said PM emission issue in response to a number of regeneration times of said first PM sensor in a predetermined period of time.

19. The diagnostic control apparatus of claim 18, further comprising:
   a fueling rate sensing means providing a fueling rate sensing signal indicative to a fueling rate of said internal combustion engine, wherein said diagnostic controller is further configured to determine said PM emission issue in response to said fueling rate sensing signal.

20. The diagnostic control apparatus of claim 18, further comprising a second PM sensor providing a second PM sensing signal indicative of a particulate matters amount in an exhaust flow upstream from said diesel particulate filter, wherein said diagnostic controller is further configured to determine said PM emission issue in response to said second PM sensing signal.

* * * * *